United States Patent [19]
Arutjunian et al.
[11] 4,288,377
[45] Sep. 8, 1981

[54] PROCESS FOR PURIFICATION OF WOOL GREASE

[76] Inventors: Norair S. Arutjunian, ulitsa Krasnaya, 143/1, kv. 35; Evgenia A. Arisheva, ulitsa Kotovskogo, 92, kv. 22, both of Krasnodar; Nikolai V. Rogachev, pereulok Sportivny, 17; Lidia G. Vasilievna, ulitsa Matrosova, 153a, kv. 57, both of Nevinnomyssk Stavropolskogo kraya, all of U.S.S.R.

[21] Appl. No.: 163,739

[22] Filed: Jun. 27, 1980

[51] Int. Cl.[3] .......... C11B 1/10; C07J 9/00
[52] U.S. Cl. .......... 260/397.25; 260/426
[58] Field of Search .......... 260/425, 426, 397.25

[56] References Cited

U.S. PATENT DOCUMENTS

| | | | |
|---|---|---|---|
| 1,194,013 | 8/1916 | Handy | 260/426 |
| 3,983,147 | 9/1976 | Senda et al. | 260/425 |

FOREIGN PATENT DOCUMENTS

| | | | |
|---|---|---|---|
| 892061 | 2/1972 | Canada | 260/426 |

*Primary Examiner*—John F. Niebling
*Attorney, Agent, or Firm*—Steinberg & Raskin

[57] ABSTRACT

A process for purification of wool grease comprising mixing the grease miscelle in a hydrocarbon solvent with an alcohol in a ratio of from 10:1 to 10:4, mixing an aqueous solution of an alkali with an alcohol in a ratio of water:alkali-alcohol of 60–75:2–5:20–35, neutralization of free fatty acids by dispersing said mixture of the grease miscelle with the alcohol in said aqueo-alcoholic solution, followed by separation of the formed phases by settling.

4 Claims, No Drawings

PROCESS FOR PURIFICATION OF WOOL GREASE

The present invention relates to the process for purification of wool grease and, more specifically, of wool grease recovered by way of washing of wool with hydrocarbon solvents or recovered from waste waters forming upon washing of wool with solutions of surfactants with the view to produce lanolin employed in the pharmaceutical industry and cosmetics.

Known in the art is a process for purification of wool grease by neutralization of the grease miscelle in a hydrocarbon solvent by means of an aqueous solution of an alkali in the presence of an alcohol.

The micelle with the grease concentration of 25% is fed to a mixer, whereinto a 20% solution of an alkali is introduced. Added to the mixer is also the hydrocarbon solvent and an aqueous solution of the alcohol. The mixture is stratified, by settling, into two layers: the upper layer comprising the neutralized miscelle, the lower layer comprising the aqueo-alcoholic soap solution (soap-stock). The neutralized miscelle containing a considerable amount of soap is subjected to a multiple washing with an aqueo-alcoholic solution. The layer of the aqueo-alcoholic soap solution is subjected to washing with a hydrocarbon solvent to recover the grease (N. V. Rogachev, "Wool Washing with Solvents", Moscow, CNIITELegprom, 1971, p. 29).

This process contemplates the use of considerable excess of a high-concentrated alkali which contributes to saponification of the grease and causes a reduced solubility of soap in the neutralizing solution. The composition of the reacting phases is determined by the diagram of the phase equilibrium for pure solvents: hexane, isopropanol and water. The actual reaction mixture contains: the miscelle, isopropanol, the aqueous soap solution and the alkali. The actual composition of the reaction system is more complicated and the composition of the existing phases corresponding to the specific ratio of the components is substantially different from the composition found by the diagram. The lasting and intensive contact of the phases under stirring and, as a result, the mutual dissolution of the components contributes to an increased dissolution of soaps in the miscelle. In this connection, the neutralized miscelle contains a considerable amount of the soap and for the production of a high-quality lanolin a repeated washing of the miscelle with the aqueo-alcoholic solution is required, whereas to ensure lower losses of the grease a repeated washing of the soap-stock with a hydrocarbon solvent is needed.

Therefore, the above-described prior art process is characterized by the use of high concentrations of alkalis thus causing saponification of the neutral grease and, hence, a reduced yield of the final product and, furthermore, a wrong selection of the ratio of the starting components, the sequence of their incorporation, as well as an intensive phase contact which results in the migration of the soap to the neutralized miscelle and an increased content of lanolin in the neutralizing solution, thus causing the necessity of repeated washings of the miscelle to reduce the content of soap therein and treatment of the neutralizing solution to reduce losses of lanolin and complicates the process technology and the equipment employed.

It is the main object of the present invention to improve quality of the desired product and increase the yield thereof.

It is another object of the present invention to simplify the process scheme and the equipment employed.

The present invention is directed to the provision, by way of variation of the process steps and selection of specific ratios of the starting components, of a process for the purification of wool grease, which would make it possible to increase the desired product yield, improve its quality, simplify the process technology and the equipment employed.

These and other objects are accomplished by that in a process for the purification of wool grease by way of neutralization of the miscelle of the grease in a hydrocarbon solvent by means of an alkali in the presence of an alcohol, in accordance with the present invention the grease miscelle in the hydrocarbon solvent is mixed with the alcohol in a ratio of from 10:1 to 10:4 and the aqueous solution of the alkali is mixed with the alcohol in a ratio of water to the alkali and to the alcohol of 60–75:2–5:20–35 respectively; then the resulting mixture of the miscelle with the alcohol is dispersed into the thus-prepared aqueo-alcoholic solution of the alkali, followed by separation of phases by settling.

It is preferable to use hexane as the hydrocarbon solvent, and isopropanol—as the alcohol.

It is preferable to use the miscelle with the grease concentration therein of from 10 to 40% by weight.

The process according to the present invention is based on the account of properties of characteristics of the system formed upon neutralization of the wool grease and creates the conditions lowering the water-absorbing capacity of the grease and increasing solubility of the resulting soaps. The neutralization is conducted under mild conditions without intensification of the process due to stirring, thus avoiding saponification of the neutral grease and lowering emulsification of the grease and migration thereof to the neutralizing solution.

The process according to the present invention is effected in the following manner.

The miscelle produced by washing of wool with a hydrocarbon solvent such as hexane or by dissolution, in a hydrocarbon solvent, of the grease recovered from the washings, is mixed with an alcohol such as isopropanol in a ratio of from 10:1 to 10:4 and an aqueous solution of an alkali is mixed with an alcohol, preferably isopropanol in a ratio of water, the alkali and the alcohol of 60–75:2–5:20–35. Said ratios ensure a minimal mutual dissolution of the components upon mixing of the phases. It is preferable to use the miscelle with the grease content therein of from 10 to 40% by weight.

The prepared miscelle is dispersed into the alkali solution, followed by phase separation by settling.

The process according to the present invention has the following advantages over the prior art:

improved quality of lanolin due to a lowered content of soap therein which is attained by the addition of the alcohol to the miscelle and the neutralizing solution in the above-specified proportions ensuring the maximum stratification of phases and a reduced migration of the soap to the neutralized miscelle;

increased yield of the final product due to the use of alkali solutions of a low concentration;

elimination of repeated washings of the miscelle and the neutralizing solution due to a reduced migration of the soap to the neutralized miscelle and losses of lanolin with the neutralizing solution;

simplified process technology and equipment.

For a better understanding of the present invention, some specific examples illustrating the process for purification of wool grease are given hereinbelow.

EXAMPLE 1

For the neutralization there are used 15 kg of a hexane miscelle containing 10% of wool grease and 10% of isopropyl alcohol. The acid number of the starting grease is 12.5 mg KOH. As the neutralizing agent use is made of an aqueo-alcoholic solution of caustic soda in the ratio of water, alcohol and alkali equal to 73.5:24:2.5.

The neutralization is conducted in a laboratory unit comprising a glass column with a thermostatting jacket. The process is conducted at the temperature of 50±5° C.

The alkali solution is placed into a column and the prepared miscelle is dispersed therein. To determine the quality characteristics of the neutralized miscelle, samples are taken after settling.

As the control use is made of a sample of the miscelle with the grease concentration therein of 25% which is neutralized by the prior art method. The miscelle is mixed in a beaker with a 20% aqueous solution of an alkali; in doing so, isopropyl alcohol is added to the reaction mixture at the rate of 40% based on the aqueous phase amount. The neutralized miscelle is subjected to washing for 5 times with a 40% aqueo-alcoholic solution.

The soap-alkali solution formed upon the neutralization is washed with hexane and the resulting miscelle is combined with the basic volume of the miscelle, whereafter samples are taken for the determination of quality characteristics of the neutralized miscelle.

The comparative data obtained in the experiments are shown in Table 1 hereinbelow. From the data of this Table it follows that the neutralization of wool grease according to the process of the present invention ensures an improved quality of the neutralized grease due to a reduced content of the soap therein by 10 times as compared to the miscelle neutralized and washed with an aqueo-alcoholic solution by the prior art process.

The process according to the present invention provides for a reduced amount of the grease wastes upon neutralization which shows an increased efficiency of this process.

EXAMPLE 2

For neutralization use is made of a hexane miscelle in the amount of 15 kg containing 27% of the grease and 20% of isopropanol. The acid number of the starting grease is 14.1 mg KOH.

As the neutralizing agent use is made of an aqueo-alcoholic solution of caustic soda with the ratio of water, alcohol and alkali is 62:35:3.

The neutralization is conducted in a laboratory unit similar to that described in Example 1 hereinabove. The process is carried out at the temperature of 50±5° C. in a manner similar to that described in Example 1.

As the control use is made of a sample similar to that described in Example 1. The test results are given in the following Table 1.

EXAMPLE 3

For the neutralization use is made of a hexane miscelle in the amount of 15 kg containing 27% of the grease and 10% of isopropanol. The acid number of the starting grease is 14.1 mg KOH. As the neutralizing agent use is made of an aqueo-alcoholic solution of caustic soda; the ratio of water, alcohol and alkali is 73.5:24:2.5 respectively.

The process is conducted as in Example 1 hereinbefore.

As the control use is made of a sample similar to that described in Example 1. The test results are shown in the following Table 1.

TABLE 1

| Characteristic | By the known process | By the process of the invention Example 1 | 2 | 3 |
|---|---|---|---|---|
| 1. Acid number of the neutralized grease, mg KOH | 0.36 | 0.32 | 0.34 | 0.35 |
| 2. Content of soap in the neutralized grease, % | 0.62 | 0.03 | 0.08 | 0.05 |
| 3. Ash content, % | 0.06 | 0.03 | 0.04 | 0.03 |
| 4. Yield of the neutralized grease, % | 90.0 | 94.0 | 93.0 | 92.5 |
| 5. Savings of the neutral grease, % | — | 4.0 | 3.0 | 2.5 |

What is claimed is:

1. A process for purification of wool grease comprising mixing the grease miscelle in a hydrocarbon solvent with an alcohol in a ratio of from 10:1 to 10:4, mixing an aqueous alkali solution with an alcohol in a ratio of water: alkali:alcohol of 60–75:2–5:20–35, neutralization of free fatty acids by dispersing said mixture of the miscelle with said alcohol in said aqueous-alcoholic alkali solution, followed by separation of the formed phases by settling.

2. A process as claimed in claim 1, wherein as the hydrocarbon solvent hexane is used.

3. A process as claimed in claim 1, wherein the grease concentration in the employed miscelle is 10 to 40% by weight.

4. A process as claimed in claim 1, wherein as the alcohol isopropanol is used.

* * * * *